US010273447B2

(12) United States Patent
Desfougeres et al.

(10) Patent No.: US 10,273,447 B2
(45) Date of Patent: Apr. 30, 2019

(54) PENTOSE-FERMENTING STRAIN WITH OPTIMIZED PROPAGATION

(71) Applicant: LESAFFRE et COMPAGNIE, Paris (FR)

(72) Inventors: Thomas Desfougeres, Neuville en Ferrain (FR); Georges Pignede, Marcq en Baroeul (FR); Jennifer Techel, Le Bizet (BE)

(73) Assignee: LESAFFRE et COMPAGNIE, Paris (FR)

( * ) Notice: Subject to any disclaimer, the term of this patent is extended or adjusted under 35 U.S.C. 154(b) by 0 days.

(21) Appl. No.: 15/116,756

(22) PCT Filed: Feb. 16, 2015

(86) PCT No.: PCT/FR2015/050364
§ 371 (c)(1),
(2) Date: Aug. 4, 2016

(87) PCT Pub. No.: WO2015/121595
PCT Pub. Date: Aug. 20, 2015

(65) Prior Publication Data
US 2016/0348064 A1 Dec. 1, 2016

(30) Foreign Application Priority Data
Feb. 17, 2014 (FR) ..................... 14 51246

(51) Int. Cl.
*C12N 1/36* (2006.01)
*C12N 15/81* (2006.01)
*C12R 1/865* (2006.01)
*C12P 7/10* (2006.01)
*C12N 9/12* (2006.01)
*C12N 9/92* (2006.01)

(52) U.S. Cl.
CPC .............. *C12N 1/36* (2013.01); *C12N 9/1205* (2013.01); *C12N 9/92* (2013.01); *C12N 15/81* (2013.01); *C12P 7/10* (2013.01); *C12R 1/865* (2013.01); *C12Y 207/01006* (2013.01); *C12Y 207/01017* (2013.01); *C12Y 503/01005* (2013.01); *Y02E 50/16* (2013.01); *Y02E 50/17* (2013.01)

(58) Field of Classification Search
CPC .... C12Y 503/01005; C12Y 207/01006; C12Y 207/01017; C12N 1/36; C12N 15/81; Y02E 50/16
See application file for complete search history.

(56) References Cited

U.S. PATENT DOCUMENTS

2010/0112658 A1* 5/2010 Hughes ............... C12N 1/18
435/161

FOREIGN PATENT DOCUMENTS

| WO | WO-2005/121337 A1 | 12/2005 |
|---|---|---|
| WO | WO-2010/000464 A1 | 1/2010 |
| WO | WO-2011/079388 A1 | 7/2011 |
| WO | WO-2012/072793 A1 | 6/2012 |
| WO | WO-2013/081700 A1 | 6/2013 |
| WO | WO-2013/178915 A1 | 12/2013 |
| WO | WO-2013/178918 A1 | 12/2013 |

OTHER PUBLICATIONS

Lee et al. 2012; Directed evolution of xylose isomerase for improved xylose catabolism and fermentation in the yeast *Saccharomyces cerevisiae*. Applied and Environmental Microbiology. 78(16): 5708-5716.*
Ma et al. 2012; Genetic engineering of the inhibitor-tolerant *Saccharomyces cerevisiae* for improved xylose utilization in ethanol production. Bioeng. Res. 5: 459-469.*
Bellissimi et al., Yeast propagation, Chapter 12 pp. 145-159 IN: Ingledew, The Alcohol Textbook: A Reference fo the Beverage, Fuel and Industrial Alcohol Industries, Nottingham University Press (2009).
Demeke et al., Combining inhibitor tolerance and D-xylose fermentation in industrial *Saccharomyces cerevisiae* for efficient lignocellulose-based bioethanol production, Biotechnology for Biofuels, 6(1):120 (2013).
Demeke et al., Development of a D-xylose fermenting and inhibitor tolerant industrial *Saccharomyces cerevisiae* strain with high performance in lignocellulose hydrolysates using metabolic and evolutionary engineering, Biotechnol. Biofuels, 6(1):89 (2013).
Hamacher et al., Characterization of the xylose-transporting properties of yeast hexose transporters and their influence on xylose utilization, Microbiology, 148(Pt. 9):2783-8 (2002).

(Continued)

*Primary Examiner* — Karen Cochrane Carlson
(74) *Attorney, Agent, or Firm* — Marshall, Gerstein & Borun LLP

(57) ABSTRACT

The present invention relates to a method for obtaining a strain capable of efficiently propagating in a low nutritive potential medium, capable of metabolizing pentoses and of resisting fermentation inhibitors, comprising the following steps; a) growth of a strain of recombinant yeast with a strain of wild yeast lacking any impairments, the recombinant yeast strain comprising at least one copy of an exogenous gene of xylose isomerase and at least one additional copy of a gene of D-xylulokinase included in the genome and linked to a single sexual characteristic of the strain, b) at least two cycles of genome shuffling by sporulation and or random hybridization, c) selection of the population obtained in step b) according to a suitability criterion of the strains to metabolize xylose, d) selection of the population obtained in step c) according to a suitability criterion of the strains to grow in a Pref type medium, a medium with low nutritive value. The invention also relates to a cell, a yeast or a strain of recombinant yeast obtained according to the method, and to the use of such a cell for the production of bioethanol.

20 Claims, 3 Drawing Sheets
Specification includes a Sequence Listing.

(56) References Cited

OTHER PUBLICATIONS

Hou, Novel methods of genome shuffling in *Saccharomyces cerevisiae*, Biotechnol. Lett., 31(5):671-7 (2009).
International Search Report, International application No. PCT/FR2015/050364, dated May 20, 2015.
Jordan et al., Plant cell walls to ethanol., Biochem. J., 442:241-52 (2012).
LaGrange et al., Engineering cellulotyic ability into bioprocessing organisms, Appl. Microbiol. Biotechnol., 87:1195-208 (2010).
Morales et al., Evolutionary role of interspecies hybridization and genetic exchanges in yeasts, Microbiol. Mol. Biol. Rev., 76(4):721-39 (2012).
Pinel et al., *Saccharomyces cerevisiae* genome shuffling through recursive population mating leads to improved tolerance to spent sulfite liquor, Appl. Environ. Microbiol., 77(14):4736-43 (2011).
Spencer et al., Hybridization of non-sporulating and weakly sporulating strains of brewer's and distiller's yeasts, J. Institute Brewing, 83(5):287-9 (1977).
Zhang et al., Improved ethanol production by a xylose-fermenting recombinant yeast strain constructed through a modified genome shuffling method, Biotechnol. Biofuels, 5(1):46 (2012).

\* cited by examiner

SEQUENCE LISTING

<160> NUMBER OF SEQ ID NOS: 5

<210> SEQ ID NO 1
<211> LENGTH: 23
<212> TYPE: DNA

```
<213> ORGANISM: Saccharomyces cerevisiae

<400> SEQUENCE: 1
agtcacatca agatcgttta tgg                                              23

<210> SEQ ID NO 2
<211> LENGTH: 23
<212> TYPE: DNA
<213> ORGANISM: Saccharomyces cerevisiae

<400> SEQUENCE: 2
gcacggaata tgggactact tcg                                              23

<210> SEQ ID NO 3
<211> LENGTH: 23
<212> TYPE: DNA
<213> ORGANISM: Saccharomyces cerevisiae

<400> SEQUENCE: 3
actccacttc aagtaagagt ttg                                              23

<210> SEQ ID NO 4
<211> LENGTH: 21
<212> TYPE: DNA
<213> ORGANISM: Saccharomyces cerevisiae

<400> SEQUENCE: 4
tagttgtcag tgcaatcctt c                                                21

<210> SEQ ID NO 5
<211> LENGTH: 22
<212> TYPE: DNA
<213> ORGANISM: Saccharomyces cerevisiae

<400> SEQUENCE: 5
tatacacata tacagcatcg ga                                               22
```

PENTOSE-FERMENTING STRAIN WITH OPTIMIZED PROPAGATION

This application is a National Stage application of International Application No. PCT/FR2015/050364, filed Feb. 16, 2015, which claims the benefit under 35 U.S.C. § 119 of European Patent Application Nos. 14154302.5, filed Feb. 7, 2014 and 14176517.2, filed Jul. 10, 2014.

INCORPORATION BY REFERENCE OF MATERIAL SUBMITTED ELECTRONICALLY

This application incorporates by reference in its entirety a computer-readable nucleotide/amino acid sequence listing identified as one 1,088 byte ASCII (text) file named "50266_SubSeqListing.txt," created Aug. 1, 2016; a deposit of biological materials ("EG10"), (a yeast strain), International Depositary Authority Accession No. CNCM I-4538, deposited on Oct. 5, 2011, with Institut Pasteur, Paris France; a deposit of biological materials ("EG20"), (a yeast strain), International Depositary Authority Accession No. CNCM I-4749, deposited on May 16, 2013, with Institut Pasteur, Paris France; a deposit of biological materials ("EG21"), (a yeast strain), International Depositary Authority Accession No. CNCM I-4829, deposited on Dec. 12, 2013, with Institut Pasteur, Paris France; a deposit of biological materials ("EGAc1"), (a yeast strain), International Depositary Authority Accession No. CNCM I-4839, deposited on Mar. 13, 2014, with Institut Pasteur, Paris France; and a deposit of biological materials ("EGAc2"), (a yeast strain), International Depositary Authority Accession No. CNCM I-4840, deposited on Mar. 13, 2014, with Institut Pasteur, Paris France. The depositary CNCM (Collection Nationale de Cultures de Microorganismes) has as its address at Institut Pasteur, 25 rue du Docteur Roux, 75724 Paris Cedex 15.

The present invention belonqs to the domain of improved yeast strains, specifically for the purpose of producing alcohols, e.g. bioethanol. The process according to the invention uses combined genetic and molecular biology techniques to generate recombinant microorganisms.

Proposing white biotechnology alternatives in order to generate biofuels is a considerable challenge in view of the costs of fossil energies, potential supply problems and environmental impacts. Plant biomass is a renewable raw material of choice for the production of biofuels within the context of sustainable development.

Context

Plant biomass means any biomass which can either correspond to excesses or by-products of agricultural and agro-industrial crops such as corn, sugar cane, wheat, sorghum, trees for carpentry and furniture, or correspond to specific cultures such as *Miscanthus gigantheus, Panicum virgatum* (switchgrass) and short and very short rotation coppices. Plant biomass is a mixture of hexose-rich cellulose, pentose-rich hemicellulose and lignin which is a polymer of hydrophobic phenolic compounds. Conventionally speaking, three steps are described for the conversion of plant biomass to bioethanol:

Pretreatment with implementation of mechanical, chemical and/or heating processes to optimize subsequent hydrolysis of the biomass or a fraction of the biomass;
hydrolysis of the biomass or a fraction of the biomass by action of reagents, solvents or enzymes with appropriate temperature and pH conditions. The objective of this hydrolysis is the release of the main fermentable monosaccharides. Enzymes used must be both stable and present acceptable hydrolysis kinetics;
the fermentation of fermentable sugars which must be robust, fast, and use all of the available sugars, i.e. both C6 (hexose) sugars and C5 (pentose) sugars.

The first and the second stage or the second and the third stage can be combined or carried out separately.

Specifically, the actual fermentation step is preceded by propagation of the microorganism that will perform fermentation, and followed by distillation. The propagation is generally carried out in the liquid phase from enzymatic saccharification, for example sequentially in two tanks, the second being significantly larger than the first. These parameters vary depending on the various industrial processes, experience and habits.

Improving the process overall may be done by combining the steps and/or improving them separately, for example in optimizing the enzymes used for hydrolysis or the microorganisms responsible for fermentation. In the latter case, it is for example useful to improve the suitability for transforming sugars, specifically by allowing the transformation of both hexoses and pentoses, and/or limit their susceptibility to inhibitors present in lignocellulose hydrolysates or fermentation solutions, such as acidity or temperature. For example, *Saccharomyces cerevisiae*, which is a yeast commonly used by producers of bioethanol, is not capable of metabolizing D-xylose but can absorb it via non-specific carriers. It is transported by hexose transporters that have a lower affinity for D-xylose than for D-glucose. Thus, it can be attractive not only to genetically modify the cell to give it the capacity to metabolize D-xylose, but also to transform it so that it absorbs said sugar more effectively.

For a review on these topics, see for example la Grange et al., 2010, Appl. Microbiol. Biotechnol., 87: 1195-1208 or Jordan et al., 2012, Biochem. J., 442: 241-252.

The present invention relates to the transformation of a cell to address metabolic deficiencies, also giving it the ability to convert D-xylose and, advantageously, to improve the property thereof of absorption of such sugar.

STATE OF THE ART

In the domain of transformation of yeasts, patent application WO 2010000464 A1 describes yeasts for fermenting C5 sugars, particularly xylose, through a transformation of said yeasts by introduction of an exogenous gene encoding a functional xylose isomerase. In this case, the xylose isomerase is derived from *Clostridium phytofermentans*.

Patent application WO 2012072793 A1 by the Applicant seeks to optimize the process of transformation of xylose by a yeast to make it compatible with industrial application. For this purpose, the application describes the introduction of expression cassettes for a gene encoding an enzyme capable of transforming any carbohydrate (including D-xylose) into xylulose (D-xylulose) and for a gene encoding an enzyme capable of transforming any pentol (including xylitol) into xylulose in just one step. This makes any strain thus modified particularly effective for growing on and/or fermenting of xylose. This document describes as an example the yeast strain deposited at the CNCM (Collection Nationale de Cultures de Microorganismes, Institut Pasteur, 25 rue du Docteur Roux, 75724 Paris Cedex 15) Oct. 5, 2011 under number I-4538.

Patent application WO 2013178915 A1, also filed by the Applicant, further improves the process by transforming yeast in order to make them both able to ferment pentoses and resistant to at least one fermentation inhibitor. Said application describes obtaining a hybrid yeast by a process combining a targeted functional aspect (conversion of the pentose) and screening on acetic acid resistance of the intermediate segregants. In this case, the cells selected by the 'acetic acid resistance' criteria have little diversity.

Finally, patent application WO 2013178918 A1, also derived from the work of the Applicant, arms to secure the method for obtaining improved yeast strains, via the integration of at least one gene of interest in a region genetically linked to a mating-type locus of expression, then crossing with MATa segregants of interest, meaning which could provide one or more phenotypic traits of interest one might wish to see combined with the genetic modification linked to the mating locus. Thus, after sporulation of the genetically modified yeast strain, the genetic change or changes segregate jointly and are all within a corresponding mating-type segregant (MAT alpha). Specifically, the use of said process for the construction of a hybrid provides certainty of a given trait of this hybrid, for example the 'ability to metabolize pentose' trait. This original method is all the more interesting in that it is applicable to any gene, for any type of possible improvement and for any yeast strain that has a haplodiplontic cycle. A haplodiplontic cycle is a reproductive cycle that alternates between a haploid and a diploid phase and during which the organism considered can multiply by mitosis both in the haploid state and in the diploid state.

Following a similar approach, Demeke et al., 2013, Biotechnology for Biofuels, 6: 89 stably integrated the expression cassettes of genes allowing the use of D-xylose and L-arabinose into the yeast genome. The hybrids obtained are also subjected to mutagenesis, a single genome shuffling cycle, then selected for their ability to use D-xylose in a medium rich in inhibitors. The authors raised the question of propagation and reported that the strain they have obtained has an average propagation rate. They suggest that the genetic changes responsible for the slower propagation rate appeared during mutagenesis and genome shuffling. This does not encourage the use of mutagenesis and/or genome shuffling to improve the fitness of a strain to multiply.

Although intended to improve industrial yeast strains, the work from the prior art has not concerned itself with a crucial step for the biofuel industrial manufacturing process: propagation. Also called multiplication, proliferation or biomass production, propagation is prior to the actual fermentation phase. The purpose is to systematically obtain an optimum quantity of biomass for fermentation. It is done by the manufacturer who will ferment a juice generated during the process, usually on the complex medium to be subjected to fermentation. The propagation juice can thus be a juice rich in pentoses, hexoses juice, or a mixture of pentoses and hexoses. This fermentation medium may be slightly diluted, enriched with nutrients, aerated to allow rapid and sufficient growth and thus allow systematically satisfactory fermentation. Mineral nutrients such as a source of nitrogen and phosphorus and such as minerals are also generally supplied and in greater proportion than in fermentation. Supplying compounds such as vitamins and organic compounds such as amino acids or purine or pyrimidine acid is avoided because it is too expensive. The manufacturer generally relies on the supply by the medium itself or by recycling fermented medium. Only supplying vitamins can be considered in order to make the supply from industrial mediums reliable since they can be variable and cause a variability in the growth taking place.

Beyond the resulting amount of growth during the propagation, the speed of the growth of the yeast is also a critical point of a successful propagation. Indeed, the speed of the growth of the yeast is going to limit the length of the propagation and limit the relative enrichment of the medium by environmental contaminants such as Lactobacilli or wild yeast. Contamination of the propagation which is too great will lead to reduced yield of ethanol production by fermentation. Even though cytostatics such as Lactrol® or the acid extracts of hops can be used to limit the growth of bacteria, having a yeast with rapid and significant growth remains key to the success of the propagation and the fermentation into which the propagations are transferred.

So having a yeast with nutritional needs reduced as far as possible which has quick and significant growth in propagation is a critical point to secure the whole of the industrial process and allow it to be ultimately profitable.

Following feedback from poor propagation capacity of one of their strains, the Applicant sought to significantly improve the ability of a yeast strain to propagate, while remaining stable genetically and keeping a good capacity to use D-xylose and resisting to the inhibitors usually present in lignocellulose 'juice'. In other words, they have sought to repair the metabolic deficiencies of a strain.

In this regard, the present invention is a method for obtaining a yeast strain suited to propagating effectively on a medium of low nutritional potential and resisting to fermentation inhibitors, while maintaining its ability to metabolize pentoses. Effectively is understood to mean by comparison between at least two strains, a reference one being thought to not produce enough biomass compatible with an industrial process in a given time. The method includes the following steps:
  a) crossing of a recombinant yeast strain with a wild yeast strain devoid of deficiencies, wherein the recombinant yeast strain includes at least one copy of an exogenous xylose isomerase gene and at least one additional copy of a D-xylulokinase gene incorporated into the genome and linked to only one of the mating traits of the strain,
  b) at least two cycles of genome shuffling by random sporulation and/or hybridization
  c) selection of the population obtained in step b) according to a criterion of ability of the strains to metabolize xylose, and
  d) selection of the population obtained in step c) according to a criterion of ability of the strains to grow in a medium poor in nitrogenous bases, a low nutritional-value medium,
noting that the two stages of selection can be reversed.

The intermediate segregants obtained after sporulation are not selected, for example on their ability of inhibitor resistance as suggested by the prior art, but they are instead submitted directly to several stages of genome shuffling without selection between mixes. It is worth noting that the ability to metabolize pentoses, essential, is preserved through the insertion of genes of interest by a method according to application WO 2013/178918 A1. The final selection according to the present invention is the lifting of the nutritional deficiencies at the origin of the poor propagation performance.

The invention also relates to a strain obtained by the process, and deposited under the Budapest treaty in the CNCM (Collection Nationale de Cultures de Microorganismes, Institut Pasteur, 25 rue du Docteur Roux, 75724 Paris Cedex 15) under the number I-4749, May 16, 2013.

Advantageously, another strain according to the invention also presents an overexpression of the GAL2 gene allowing a better entry of xylose into the cell. Overexpression is made possible by the addition of an extra copy of this gene, which is additionally made dependent on the constituent pADH1 promoter. The latter usually controls the expression of the ADH1 gene. The 'child' strain thus obtained was deposited under the Budapest treaty in the CNCM (Collection Nationale de Cultures de Microorganisms, Institut Pasteur, 25 rue du Docteur Roux, 75724 Paris Cedex 15) number I-4829, Dec. 12, 2013.

The invention relates also to the use of a strain according to the invention to transform sugars, particularly hexoses and pentoses, into ethanol.

To ensure the effective propagation of the strain obtained by the process according to the invention, inventors have defined various 'minimum' media.

A minimum medium is a medium comprising a source of carbon (CxHyOz), a source of mineral nitrogen, a source of potassium, a source of phosphorous, a source of sulfur, a source of magnesium, a source of calcium, a source of iron, a source of trace elements and water. It is a medium of low nutritional value.

Table I below brinqs together the various media used by the inventors: the low nutritional potential medium, poor in nitrogenous bases, used in the process according to the invention, is the "Pref" medium. This medium may be a minimal medium for strains according to the invention, but proves to be a sub-minimal medium for strains that do not meet the invention.

TABLE I

Culture media

| | YFC (g/L) | YFX (g/L) | YFI1 (g/L) | Pref. Medium (g/L) |
|---|---|---|---|---|
| Distilled water qs | 1000 | 1000 | 1000 | 1000 |
| Glucose | 58 | 0 | 150 | 0 |
| Xylose | 25 | 70 | 0 | 20 |
| YE type J | 0 | 5 | 5 | 0 |
| $(NH_4)PO_4$ | 0 | 4.7 | 4.7 | 0 |
| $(NH_4)_2SO_4$ | 0 | 0 | 0 | 5 |
| Protein Hydrolysate | 0 | 0 | 0 | 3 |
| Urea | 3 | 0 | 0 | 0 |
| Phosphoric acid | 0.85 | 0 | 0 | 0 |
| Citric acid | 0 | 11.4 | 11.4 | 0 |
| Trisodium citrate | 0 | 13.5 | 13.5 | 0 |
| Acetic acid | 5 | 0 | 4 | 0 |
| $ZnSO_4$ | 0.021 | 0.021 | 0.021 | 0.04 |
| $MgSO_4\ 7H_2O$ | 1 | 1 | 1 | 0.5 |
| $KH_2PO_4$ | 0 | 0 | 0 | 1 |
| NaCl | 0 | 0 | 0 | 0.1 |
| $CaCl_2$ | 0 | 0 | 0 | 0.1 |
| $H_3BO_3$ | 0 | 0 | 0 | 0.005 |
| $CuSO_4\ 5\ H_2O$ | 0 | 0 | 0 | 0.06 |
| KI | 0 | 0 | 0 | 0.001 |
| $MnSO_4\ H_2O$ | 0 | 0 | 0 | 0.004 |
| $Na_2MoO_4\ 2H_2O$ | 0 | 0 | 0 | 0.002 |
| $FeCl_3$ | 0 | 0 | 0 | 0.0002 |
| Folic acid | 0 | 0 | 0 | 0 |
| Thiamine | 0.018 | 0.018 | 0.018 | 0.07 |
| Pyridoxine | 0.0053 | 0.0053 | 0.0053 | 0.002 |
| Biotin KOH | 0.0018 | 0.0018 | 0.0018 | 0.002 |
| Pantothenate | 0.0038 | 0.0038 | 0.0038 | 0.002 |
| Nicotinic Acid | 0.016 | 0.016 | 0.016 | 0.05 |
| Mesoinositol | 0.05 | 0.05 | 0.05 | 0.2 |
| Riboflavin | 0.001 | 0.001 | 0.001 | 0.002 |
| Para aminobenzoate | 0.0012 | 0.0012 | 0.0012 | 0.002 |
| Mono-sorbate oleate | 1 | 1 | 1 | 0 |

YE = yeast extract

We also mention that:
Pref medium complemented with 3 g/L of hydrolysate of RNA of *Candida utilis*, hydrolyzed by addition of RNase A to 30 µg/L, referred to as Pref+nitrogenous bases in the rest of the text and figures;

YF12 medium containing: yeast extract 10 g/kg, Bacto-Peptone 10 g/kg, glucose 55 g/L, xylose 45 g/L, acetate 4 g/L, adjusted to pH 4.4;
YEG medium containing: yeast extract 10 g/L, glucose 20 g/L, and agarose 20 g/L.

Then, the assumption is that the resulting strain will have the ability to propagate effectively in the complex media of manufacturers who will use it to produce bioethanol.

The following definitions are given in order to better understand the invention.

The expression 'Yeast strain' refers to a relatively homogeneous population of yeast cells. A yeast strain is obtained from the isolation of a clone. A clone gives birth to a population of cells obtained from a single yeast cell.

Segregation corresponds to the situation during which, at the end of meiosis, the ploidy level is reduced. By extension, a segregant is a viable cell coming from meiosis of a cell of a ploidy level greater than 1.

The expression 'derived yeast strain' refers to a yeast strain derived by one or more crosses and/or by mutation and/or by genetic transformation.

A yeast strain derived by crossing can be obtained by cross-breeding of a yeast strain according to the invention with the same yeast strain, with another yeast strain according to the invention, or with any other yeast strain (provided that it can be crossed, by which the person skilled in the art understands that it is homozygous for the MAT locus and that there is no mutation in the STE genes).

A yeast strain derived through mutation can be a yeast strain which has undergone at least one spontaneous mutation in the genome thereof or at least one mutation induced by mutagenesis. The mutation(s) of a derived strain may be silent or not.

The expression "mutagenesis" designates the process of appearance of a mutation. Classically, two methods are possible: random mutagenesis, and insertional or directed mutagenesis. The first consists of the application of physical treatment (e.g. UV radiation) or treatment by chemical mutagenic agents, which will randomly induce mutations in the genome of the organism studied. The second will use molecular biology methods to produce a specific modification (i.e. promoter, gene, terminator, etc.) either in a region of the genome or on a specific locus. Locus is used to mean a specific and invariable physical location on a chromosome.

A yeast strain derived by genetic transformation is a yeast strain in which a DNA sequence was introduced that is preferably supplied by a plasmid or incorporated directly into the genome.

Hexoses is used to mean sugars with 6 carbon atoms, also called C6 sugars or more simply C6, used as carbon source. The main representatives of hexoses in monomer form are glucose, fructose, and galactose. By analogy, pentoses are sugars with 5 carbon atoms, also called C5 sugars or C5. The main monomer representatives of pentoses are D-xylose and L-arabinose.

Propagation refers to multiplication, proliferation or biomass production which will serve to inoculate the fermentation medium. It can be done on natural medium, for example from the transformation of plant biomass, or rich or poor synthetic medium. Generally, multiplication will be fast on a rich medium and less effective on a poor medium, requiring strong metabolic capabilities from the cell to overcome the low nutritional value (or deficiencies) of the medium. Lignocellulose hydrolysate from the transformation of plant biomass is a complex environment which can be a juice containing primarily pentoses, a juice containing primarily hexoses or a juice containing a mixture of hexoses and pentoses. From an industrial point of view, a 'rich' synthetic medium would certainly be the most effective choice for propagation but it would not be economically viable. A minimal medium, i.e. comprising the bare minimum would be more effective but defining its composition is not simple. For these reasons and for reasons of continuum of the industrial process, propagation is most often performed on the composition resulting from the previous step, in other words on lignocellulosic juice. For a review, see Bellissimi E, Richards C: Yeast propagation. In The alcohol textbook, a reference for the beverage, fuel and industrial alcohol industries. 5th edition. Edited by Ingledew W M, Kelsall D R, Austin G D, Kluhspies C. Nottingham: University Press; 2009:145-159.

Metabolic deficiency of a strain is understood to mean a failure of one or more metabolic pathways generating defects in growth or fermentation by yeast. Auxotrophy is understood to mean an inability to produce a metabolic intermediate and essential for the development of yeast on a given medium, i.e. a metabolic defect that means the strain will not grow if all nutrients that are essential thereto are not provided exogenously.

A prototrophic yeast strain is a strain able to grow on a minimal medium. In particular, a prototrophic yeast strain according to the invention is capable of synthesizing all the nitrogenous bases necessary for its growth.

Inhibitors is understood to mean the inhibitors present ab initio in lignocellulosic hydrolysates or formed during alcoholic fermentation, which include phenolics, furfural and its derivatives, hydroxy-methyl furfural and its derivatives, or even weak acids such as acetic acid, formic acid or lactic acid. It is also known that these inhibitors are harmful to the performance or even the survival of yeast. Alternatively, osmotic pressure, pH (especially highly acidic), temperature (greater than 35° C.), or the ethanol produced may also inhibit or at least limit the fermentation capacity of a strain.

A yeast strain able to metabolize xylose is a yeast strain capable of converting xylose into ethanol, i.e. capable of fermenting xylose.

The conversion of xylose into ethanol results from the direct or indirect isomerization of xylose into xylulose, followed by the use of the xylulose obtained in that way in the non-oxidative part of the pentose phosphate pathway.

A yeast strain able to metabolize xylose within the meaning of the invention refers to a yeast strain which converts at least 70%, preferably at least 80% and more preferably at least 90% of the xylose into ethanol in 60 hours in a fermentation medium comprising 55 g of glucose and 45 g of xylose per kg, in anaerobic conditions.

The inoculation with the yeast strain used to measure the percentage of xylose converted to ethanol is preferably 0.25 g dry matter/kg of fermentation medium.

The 60 hour duration is calculated from the inoculation of the fermentation medium with the yeast strain.

The fermentation medium used to measure the percentage of xylose converted to ethanol should preferably be a synthetic medium.

A synthetic medium is a medium whose exact chemical composition is known.

Fermentation should be conducted preferably at 32° C. under medium stirring, for example 90 rpm.

The stirring is moderate so as to not be oxygenating.

The pH of the medium should be controlled, e.g. by the buffering power of an acid/base pair, e.g. the acetic acid/acetate buffering power in the YFGX medium.

The amount of ethanol present in the fermentation medium is measured by any appropriate means known to the person skilled in the art.

It can be a direct measurement of the ethanol produced or an indirect measurement through a parameter related to ethanol production, such as the loss of mass.

For example, the production of alcohol may be measured by chromatography, including HPLC (High Performance Liquid Chromatography), an enzymatic kit (for example the determination of ethanol by Boehringer kit), or a determination by potassium dichromate.

The amount of xylose in the fermentation medium is measured by any appropriate means known to the person skilled in the art, preferably by chromatography, in particular HPLC.

By using a fermentation medium containing both glucose and xylose, the conversion of xylose to ethanol from a comparable quantity of biomass can be assessed for the various yeast strains evaluated. Indeed, yeast strains first ferment glucose from the glucose and xylose mixture, then glucose and xylose, and then xylose.

The ability to metabolize xylose in the presence of at least one fermentation inhibitor is called resistance to said fermentation inhibitor.

DETAILED DESCRIPTION OF THE INVENTION

Figure 1:
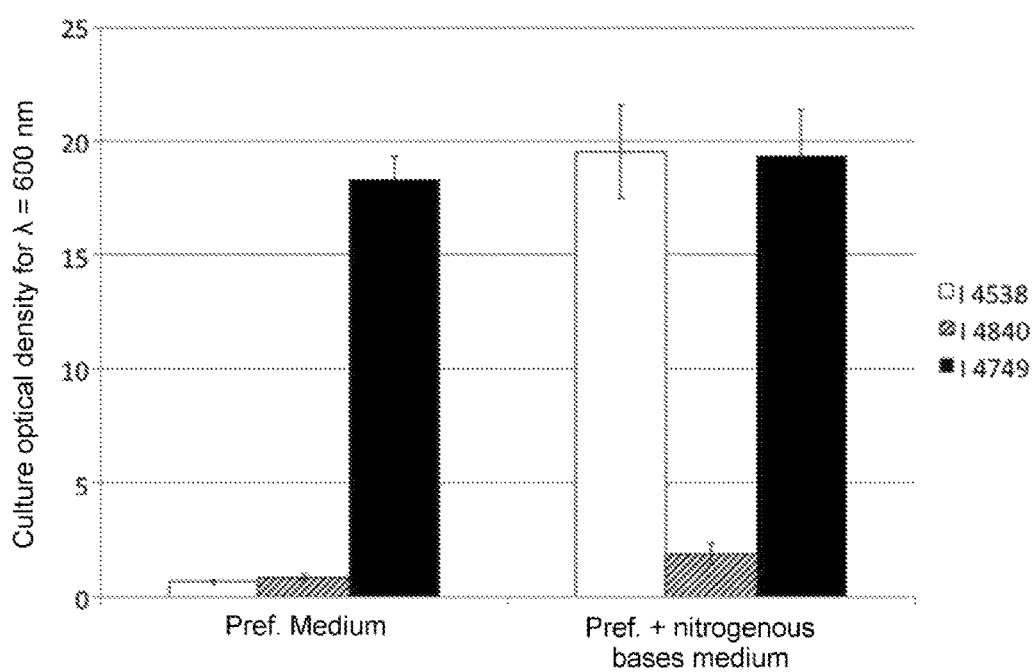
FIG. 1 shows the respective propagation of strain I-4538 (recombinant parent strain, deposited at the CNCM on Oct. 5, 2011), EGAc1 deposited at the CNCM on Mar. 13, 2014, under reference I-4839 (wild parent strain) and I-4749 (strain according to the invention, deposited at the CNCM on May 16, 2013) on Pref and Pref+nitrogenous bases media with low nutritional value.

Initially, it appeared that the strain I-4538 had metabolic deficiencies which negatively impacted the efficiency of the propagation thereof on complex media. Said strain I-4538 is one of the strains obtained according to patent application WO 2012072793 A1, comprising at least one copy of an exogenous gene encoding a xylose isomerase, and one copy of an exogenous gene encoding a xylitol dehydrogenase. It also comprises at least one additional copy of the XKS1 gene and genes for the pentose-phosphate pathway. In practical terms, this strain has a good capacity to metabolize xylose and resists to fermentation inhibitors resulting from the hydrolysis of biomass such as phenolic products, furfural and acetic acid. Thus, the propagation phase on a medium poor in nitrogenous bases additionally containing xylose was analyzed in order to be subsequently improved. It appeared that hydrolyzed RNA, otherwise known as nitrogenous bases, was very favorable to the growth of strain I-4538. Interestingly, this auxotrophy is not present on a medium containing glucose, which indicates that the biosynthetic pathways are functional, but poorly regulated in a medium containing xylose. Since yeast is not naturally able to metabolize this sugar, it is possible that the expression of the genes required for the synthesis of the nitrogenous bases is not sufficient. Moreover, the various stages of genetic transformations and UV radiation leading to obtaining the strain are likely responsible for these deficiencies.

As a first step, strain I-4538 is hybridized with a wild strain with no deficiency (referenced strain EGAc1 deposited at the CNCM on Mar. 13, 2014, under reference I-4839 in the examples and figures). A wild strain refers to a non-genetically modified strain. This step has led to a hybrid whose metabolic deficiencies were partly repaired but which had lost a significant part of the capacity to ferment xylose rapidly.

The hybridization step is carried out according to conventional techniques, such as those taught in Chapter 7, "Sporulation and Hybridization of Yeast" by R. R. Fowell, in the reference work "The Yeasts", Volume 1, published by A. H. Rose and J. S. Harrison, 1969-Academic Press.

A second step is a random genome recombination, more specifically by four cycles of genome shuffling. The cycles are carried out without selection between two steps. This step is done according to a method adapted from Hou, 2009, Biotechnol. Lett., 31: 671-677.

The resulting population is selected according to a criterion of ability to metabolize xylose, then according to a criterion of ability to multiply on a low nutritional value medium, especially the ability to dispense with nitrogenous bases in the propagation medium.

The two selection criteria can be inverted. In other words, it is possible to select first the ability to multiply in a deficient medium then select the ability to ferment xylose or first on the capacity to ferment xylose then on the ability to multiply in a deficient medium.

The resulting strain was deposited at the CNCM (Collection Nationale de Cultures de Microorganismes, Institut Pasteur, 25 rue du Docteur Roux, 75724 Paris Cedex 15) under number I-4749.

Interestingly, the removal of auxotrophy towards the nitrogenous bases on a medium containing xylose as the sole carbon source is transmissible to the strains that descend in a straight line from strain I-4749. In that way, various strains, among them the deposited strain I-4829, were obtained from strain I-4749. Indeed, it was observed that the protein Gal2p is a transporter of hexoses also capable of transporting xylose (Hamacher et al. 2002, Microbiology, 148: 2783-2788). Thus, improving the capture of xylose by a yeast strain, e.g. Saccharomyces cerevisiae, that could have been made capable of fermenting xylose, is attractive. For this reason, a copy of the gene GAL2, made dependent on a strong and constitutive promoter (pADH1), was introduced into the genome of the strain. It encodes for a channel that promotes the entry of xylose into cells. This strain is a yeast strain according to the invention. The strain obtained by this additional genetic modification has been deposited at the CNCM (Collection Nationale de Cultures de Microorganismes, Institut Pasteur, 25 rue du Docteur Roux, 75724 Paris Cedex 15) under reference I-4829.

Yeasts are obtained by culture of a yeast strain according to the invention or of a yeast strain derived according to the invention, in particular as described in the book of reference "Yeast Technology", 2nd edition, 1991, G. Reed, and T. W. Nagodawithana, published by Van Nostrand Reinhold, ISBN 0-442-31892-8.

The multiplication of yeasts, on an industrial scale, generally includes at least the first two steps from the following set of steps:
multiplication of a yeast strain in several stages, first in semi-anaerobiosis, and then in aerobiosis,
separation of the yeast produced from its culture medium by centrifugation, in order to obtain a liquid yeast cream containing between about 12 and 25% of dry matter, or even a higher quantity of dried matter if the yeast cream is mixed with osmolytic products,
filtration of the liquid yeast cream obtained, in general on a rotary vacuum filter, to get a fresh dehydrated yeast containing 26-35% dry matter,
mixing of said fresh dehydrated yeast in order to obtain a homogeneous mass,
extrusion of the yeast thus obtained, in order to obtain:
a pressed yeast in the form of fresh cake yeast or crumbled fresh yeast containing about 30% dry matter, or
a yeast in the form of particles, granules in general, if the yeast is intended to be dried,
possibly controlled drying, in a current of hot air, e.g. by fluidization, particles of yeast obtained by extrusion in order to obtain dry yeast.

The drying step is preferably fast controlled drying in the presence of an emulsifier.

Among the emulsifiers which can be used during the drying stage, it is possible to choose sorbitan monostearate, used for example at a concentration of about 1.0% (by weight over the weight of dry yeast).

Yeasts according to the invention can be used in any possible form.

For example, the subject of the present invention is a yeast such as defined above, characterized in that it is in the form of yeast cream, pressed yeast, dry yeast or frozen yeast.

The subject of the present invention is also a method of producing at least one fermentation product comprising a step of fermentation in anaerobic or semi-anaerobic conditions by a yeast such as defined above in a fermentation medium.

The fermentation product is especially chosen from ethanol, a metabolite obtained from ethanol or a secondary metabolite.

A preferred fermentation product according to the invention is ethanol.

Ethanol production results from alcoholic fermentation.

The person skilled in the art knows how to determine the appropriate conditions for alcoholic fermentation.

For example, one can refer to the alcoholic fermentation conditions described in the reference book "Yeast Technology", 2nd edition, 1991, G. Reed and T. W. Nagodawithana, published by Van Nostrand Reinhold, ISBN 0-442-31892-8.

The fermentation medium includes the following elements: at least one source of fermentable carbon, at least one source of nitrogen, at least one source of sulfur, at least one source of phosphorus, at least one source of vitamins and/or at least one source of minerals.

The carbon source is for example supplied in the form of a sugar immediately available to the yeast, a pentose such as xylose, glycerol, ethanol and/or a combination thereof.

A sugar immediately available to the yeast is for example a simple sugar of glucose, fructose or galactose type, a disaccharide of sucrose type and/or a mixture of these sugars.

The carbon source can be supplied in the form of a glucose syrup, a fructose syrup, a saccharose syrup, molasses, hydrol (spent mother liquor from 2nd sugar crystallization), a hydrolysate of all or part of a plant material and/or a mixture thereof.

The nitrogen source is for example provided in the form of ammonium sulfate, ammonium hydroxide, di-ammonium phosphate, ammonia, urea, and/or a combination thereof.

The sulfur source is for example provided in the form of ammonium sulfate, magnesium sulfate, sulfuric acid, and/or a combination thereof.

The source of phosphorus is for example provided in the form of phosphoric acid, potassium phosphate, di-ammonium phosphate, mono-ammonium phosphate, and/or a combination thereof.

The source of vitamins is for example provided in the form of molasses, yeast hydrolysate, a solution of pure vitamins or a mixture of pure vitamins and/or a combination thereof.

The source of vitamins supplies the yeast with all vitamins in amounts at least equivalent to those recommended in reference books. Several sources of vitamins can be combined.

The source of minerals is for example provided in the form of molasses, a mixture of mineral salts and/or a combination thereof.

The mineral source supplies yeast with all macronutrients and trace minerals in amounts at least equivalent to those recommended in reference books. Several mineral sources can be combined.

The same substance may supply several different elements.

The subject of the present invention is a process as defined above for the production of at least one fermentation product, preferably ethanol, comprising a step of fermentation in anaerobic or semi-anaerobic conditions, by a yeast such as defined above in a fermentation medium comprising xylose and/or at least one fermentation inhibitor. Preferentially, the fermentation medium includes at least one hydrolysate of all or part of a plant material.

A hydrolysate of all or part of a plant material can be obtained by a step of pre-treatment of the plant material, e.g. at a high temperature and in the presence of acids or organic solvents, which could be followed by a total or partial hydrolysis of sugar polymers, by enzymatic and/or chemical and/or thermal routes.

The hydrolysate of all or part of a plant material therefore includes a mixture of sugars from the hydrolysis of sugar polymers, such as cellulose, hemicellulose, and starch.

The fermentation inhibitor is for example selected among an organic acid, furfural, HMF (hydroxy-methyl-furfural), one or more phenolic compounds and osmotic pressure.

The organic acid is for example selected among acetic acid, lactic acid, formic acid and levulinic acid.

The subject of the present invention is also the use of a yeast such as defined above for the production of at least one fermentation product, preferably in a fermentation medium containing xylose and at least one fermentation inhibitor. In other words, the use of a yeast according to the invention allows the conversion and the metabolism of a material of plant origin comprising xylose.

The fermentation product is as defined above.

Preferably, the fermentation product is ethanol.

The fermentation medium is as defined above.

The following examples are intended to better understand the invention but are in no way limiting.

EXAMPLES

Crossing a Recombinant Strain with a Wild Strain then Sporulation.

The recombinant strain deposited at the CNCM (Collection Nationale de Cultures de Microorganismes, Institut Pasteur, 25 rue du Docteur Roux, 75724 Paris Cedex 15) under number I-4538 was crossed with a wild strain, in this case the strain of the applicant EGAc1 (I-4839). This step was carried out according to conventional techniques, such as those taught in Chapter 7 "Sporulation and Hybridization of Yeast" by R. R. Fowell, in the reference work "The Yeasts", Volume 1, edited by A. H. Rose and J. S. Harrison, 1969-Academic Press.

The EGAc2 strain deposited at the CNCM under reference I-4840 on Mar. 13, 2014 was thus obtained. This strain showed good performance metabolizing xylose and only partially repaired deficiencies. Indeed, the quality of the propagation remained poor on a low nutritional value medium comprising essentially xylose and a protein hydrolysate.

Sporulation was carried out in liquid media without nitrogen source and containing a non-fermentable carbon source, preferably an acetate salt, ideally potassium acetate.

Establishment of a Rapid Method of Segregant Enrichment

Insofar as it did not seem possible to obtain 100% of segregants, it was necessary to eliminate the diploids that had not completed meiosis.

To do this, the asci dissection method is usually implemented but has the disadvantage of being very time-consuming. Thus, the Applicant has used a distinctive characteristic of spores, namely that they are renowned for their greater resistance to temperature (Williams, 1936, J. Bacteriol., 32 (6): 589-597), the lack of certain nutrients (Ho & Miller, 1978, Can. J. Microbiol., 24 (3): 312-320) or some organic solvents (Dawes and Hardie, 1974, Mol. Gen. Genet., 131 (4): 281-289).

In this case, a method based on ether enrichment described by Dawes and Hardie (supra) was used. Indeed, this approach is simple and effective.

Indeed, due to the formation of the segregants in the membrane of the diploid, they are not surrounded by one phospholipid bilayer, but two. On the other hand, the diploids have only one. When it is used with an optimal contact time (variable from one strain to another) ether breaks down diploid membranes. The ether is therefore attractive for two reasons. Firstly, it kills the diploids without affecting the segregants if the contact time is not too long. On the other hand, it degrades the phospholipid bilayer of the asci that holds the segregants in the form of tetrads, of which the result is releasing them and allowing them to germinate.

This method was suited to the industrial strains of the Applicant. The contact time between the yeast suspension and the ether must then be closely monitored. To do this, 2 mL of ether is brought into contact with 2 mL of the yeast suspension containing approximately $2 \times 10^7$ sporulation structures. Sporulation is obtained after 5 days in sporulation conditions. The whole is then vortex stirred during total contact time ranging from 30 seconds to 2 minutes.

An aliquot containing 1000 cells/mL is immediately spread at the 100 µL/dish level on a medium containing:

Yeast extract 5 g/L, glucose 20 g/L, agar 30 g/L, water qs 1 L. After 48 hours of growth, the colonies are used to make a "PCR on colony" by using SEQ ID No 1, SEQ ID No 2 and SEQ ID No 3 primers corresponding respectively to the Mat1, Mat2 and Mat3 primers such as described in application WO2013/178918 A1. This PCR analysis arms to differentiate haploid strains from diploid strains.

Different contact time trials show that, in the case of strain EGAc2 (I-4840), exposure of 1 minute is sufficient for enrichment to over 98% in haploid strains.

Establishment of the Bulk Hybridization Protocol

New hybrids were generated from suspensions enriched in segregants by performing a bulk-phase hybridization. To do this, 1 mL of the suspension of segregants was inoculated in 50 mL of YPG medium containing yeast extract 10 g/L, Bactopeptone 20 g/L, glucose 20 g/L and distilled water qs 1 L. After 16 hours in this medium, microscopic observation confirmed the formation of zygotes. In order to promote the development of these hybrids, every 24 hours, 200 µL of the culture was inoculated into 50 mL of fresh YEG medium. After 5 days of subculture, the new hybrids can be reintroduced in a mass sporulation cycle.

In order to ensure the efficiency of this bulk hybridization step, 100 cells are distributed per Petri dish containing YEG. The reproduction characteristic of the cells constituting 139 of the formed colonies were then analyzed by PCR on DNAg. These colonies were selected randomly. The PCR performed using primers SEQ ID No 1, SEQ ID No 2 and SEQ ID No 3 (supra) showed that only 2 colonies of the 139 tested were haploid.

Validation of Genome Shuffling in the Resulting Population of Hybrids
Analysis of the Genotype of the Starting Hybrid.

One of the methods to validate the quality of genome shuffling consists of studying the distribution of alleles from two loci linked to the gene GRE3. Indeed, the deletion of both copies of the gene GRE3 corresponding to a "gre3 null" genotype was conducted in C5 strains leading to strain I-4538. This disruption was transmitted to the strain EGAc2 (I-4840) which, because of the non-deletion of GRE3 in EGAc1 (I-4839), is therefore heterozygous.

The possible transmission of this trait in the derived segregants of strain EGAc2 (I-4840) has been sought. To do this, PCR were done with a pGRE3 promoter-specific primer TAGTTGTCAGTGCAATCCTTC (SEQ ID No 4) and a tGRE3 terminator-specific primer TATACACATATACAG-CATCGGA (SEQ ID No 5) of GRE3. The results showed that it was possible to differentiate wild copies of the gene GRE3 which give a 1200 bp (base pair) fragment, from deleted forms that give a 200 bp fragment.

So some segregants of strain EGAc2 (I-4840) presented exclusively the deleted version while others presented only the wild copy of GRE3. More surprisingly, a third category of segregants had 2 copies of the gene GRE3, one wild type, and the other deleted. This result is explained by the fact that there are not two, but four copies of the GRE3 gene in strain EGAc1 (I-4839). In this case, there are two copies of GRE3 in the EGAc1 segregant (I-4839) which gave EGAc2 (I-4840). So the genotype of strain EGAc2 (I-4840) is the following:

$$\frac{GRE3}{gre4\Delta}; \frac{GRE3}{-}$$

Such a genotype is due to the presence of GRE3 at two different loci in strain EGAc1 (I-4839) against 1 single locus in the strain I-4538. In addition in strain I-4538, the GRE3 gene has been deleted. Thus, among 137 diploid strains obtained at the end of a first round of genome shuffling of strain EGAc2 (I-4840), the GRE3 gene and the dispersion of alleles among hybrids have been studied.

Determination of Expected Segregants

In relation to the GRE3 genotype, a hybrid like EGAc2 (I-4840) can therefore give 4 types of segregants. These segregants are listed in table II below. The segregants with genotype gre3Δ; —and GRE3; GRE3 are so-called parental genotypes because all their alleles originate from a single parent. In contrast, segregants GRE3; —and gre3Δ; GRE3 are referred to as recombinant. For each case, there is a MATa form and a MAT alpha form.

Table II: Genotype of the Various Obtainable Segregants

TABLE II

Genotype of the various obtainable segregants

| Starting hybrid | Segregants | |
|---|---|---|
| Mat a/Mat α | Mat a | Mat α |
| $\frac{GRE3}{gre3\Delta}; \frac{GRE3}{-}$ | GRE3; GRE3 | gre3Δ; — |
| | GRE3; — | gre3Δ; GRE3 |
| | gre3Δ; GRE3 | GRE3; — |
| | gre3Δ; — | GRE3; GRE3 |

A way to analyze the quality of genome shuffling consisted of looking for the distribution of alleles from the parental hybrid in the segregants. Thus, under the assumption that the loci are independent, the probability of obtaining a parental segregant is equal to that for a recombinant segregant.

However, the approach seeks to work without selecting the segregants. Indeed, the purpose was to determine the spores that had actually been involved in the formation of the hybrids. The genetic analysis was therefore performed from the hybrids.

Analysis of Resulting Hybrids

Hybrids which may result at the end of this genome shuffling are shown in table III. The genotypes of each type of hybrid are referenced in the corresponding box. These genotypes are divided into 3 groups with respect to the PCR profiles with pGRE3 (SEQ ID No 4) and tGRE3 (SEQ ID No 5) primers:

Group 1: A single band at a 200 BP size (text in the table not italicized or bolded)
Group 2: Two bands of 200 BP and 1200 BP (text in the table italicized)
Group 3: A single band of 1200 BP (text in the table italicized and bolded)

Table III: Genotype of the various hybrids that can be obtained. Row 2 and column 2, these are segregants, the other boxes are hybrids.

TABLE III

Genotype of the various hybrids that can be obtained. Row 2 and column 2, these are segregants, the other boxes are hybrids.

| | | Mat α | | | |
|---|---|---|---|---|---|
| | | gre3Δ; — | gre3Δ; GRE3 | GRE3; — | GRE3; GRE3 |
| Mat a | gre3Δ; — | $\frac{gre3\Delta}{gre3\Delta}; \frac{-}{-}$ | $\frac{gre3\Delta}{gre3\Delta}; \frac{GRE3}{-}$ | $\frac{GRE3}{gre3\Delta}; \frac{-}{-}$ | $\frac{GRE3}{gre3\Delta}; \frac{GRE3}{-}$ |

TABLE III-continued

Genotype of the various hybrids that can be obtained. Row 2 and
column 2, these are segregants, the other boxes are hybrids.

| | Mat α | | | |
|---|---|---|---|---|
| | gre3Δ; — | gre3Δ; GRE3 | GRE3; — | GRE3; GRE3 |
| gre3Δ; GRE3 | $\frac{gre3\Delta}{gre3\Delta};\frac{-}{GRE3}$ | $\frac{gre3\Delta}{gre3\Delta};\frac{GRE3}{GRE3}$ | $\frac{GRE3}{gre3\Delta};\frac{-}{GRE3}$ | $\frac{GRE3}{gre3\Delta};\frac{GRE3}{GRE3}$ |
| GRE3; — | $\frac{gre3\Delta}{GRE3};\frac{-}{-}$ | $\frac{gre3\Delta}{GRE3};\frac{GRE3}{-}$ | $\frac{GRE3}{GRE3};\frac{-}{-}$ | $\frac{GRE3}{GRE3};\frac{GRE3}{-}$ |
| GRE3; GRE3 | $\frac{gre3\Delta}{GRE3};\frac{-}{GRE3}$ | $\frac{gre3\Delta}{GRE3};\frac{GRE3}{GRE3}$ | $\frac{GRE3}{GRE3};\frac{-}{GRE3}$ | $\frac{GRE3}{GRE3};\frac{GRE3}{GRE3}$ |

Group 1 of hybrids can be easily identified because they present a PCR profile comparable to that of the I-4538 strain when the pGRE3 and tGRE3 primers are used. It is worth noting that all hybrids with this genotype are from the MATa; gre3Δ; —and MAT alpha; gre3Δ; —segregants. Under the assumption of a genetic independence, these hybrids should represent 1/16 or 6.25% of the population. To test this assumption, the genotypes of the 137 previously mentioned hybrids were analyzed by PCR. The results are shown in table IV below.

Table IV: Results of PCR Analysis of the Genotype of the Resulting Hybrids

TABLE IV

Results of PCR analysis of the genotype of the resulting hybrids

| Genotypic group (PCR) | Number of hybrids | Proportion of the population | Proportion expected if the 2 GRE3 loci are independent |
|---|---|---|---|
| Group 1 1 band at 200 BP | 16 | 11.6% | 6.25% (1/16) |
| Group 2 2 bands at 200 and 1200 BP | 89 | 64.5% | 68.8% (11/16) |
| Group 3 1 band at 1200 pb | 32 | 23.3% | 25% (4/16) |

The over-representation of the hybrids from Group 1 (11.6% instead of 6.25%) shows that the two loci of GRE3 are not independent. In other words, this means that in meiosis, the probability of having a parental-type segregant is greater than having a recombinant type segregant. This result furthermore allows determination of the genetic distance in cM. This genetic distance is obtained via the following equation:

$$\text{Genetic distance (cM)} = \left(\frac{\text{number of recombinant segregants}}{\text{number of total segregants}}\right) \times 100$$

In this analysis, the total number of segregants is the number of hybrids multiplied by 2 (being 274).

The number of recombinant segregants is obtained by subtracting the number of parental segregants from the total number of segregants. As shown above, hybrids from group 1 consist exclusively of parental segregants. This implies that the probability of having gre3Δ; —parental segregants is equal to the square root of the probability of having a hybrid from Group 1. In addition, the parental segregants are equiprobable during meiosis. The number of recombinant segregants can therefore be determined by the following equation:

$$\text{number of recombinant segregants} =$$
$$\text{total number of segregants} - \text{number of parental segregants}$$

with:

$$\text{number of parental segregants} =$$
$$\text{total number of hybrids} \times 4 \times \sqrt{\frac{\text{number of hybrids in Group 1}}{\text{total number of hybrids}}}$$

Thus, the number of parental segregants is 186 and therefore the number of recombinant segregants is 88. This result implies that the genetic distance between two loci would be 32 cM. This genetic distance calculation serves to measure the probability of having each type of segregants.

Estimate of the Number of Starting Cells Found in the End Population

An important point related to the measurement of the quality of the diversification of the population is the determination of the number of starting hybrids which survived the entire treatment to stay in the final population. It is possible to estimate their number based on the results of the determination of the GRE3 genotype. Indeed, cells whose PCR profile presents two bands (200 BP and 1200 BP) are either hybrids obtained by genome shuffling, or starting cells that were not killed during the enrichment with ether.

Strains of Group 2=real hybrids of group 2+surviving starting cells

The results obtained in the preceding paragraph allow determination of both the number of real hybrids from Group 2 and the number of strains from Group 2.

To determine the number of real hybrids from Group 2, the proportion of each type of hybrid that makes up this group must be added together. Table V below lists various hybrids, as well as the probability of obtaining them. The probability of obtaining a type of hybrid is based on the product of the probabilities of obtaining the two segregants which go into it. It is indicated in the previous sub-section that the parental segregants represent 68% of the segregants (or 34% for each parental segregant). Consequently, the recombinant segregants represent 32% of all segregants (i.e. 16% for each recombinant segregant).

Table V: Probability of obtaining each type of hybrid. The code for the hybrids of group 1, group 2 and 3 respectively is identical in tables III and IV.

TABLE V

Probability of obtaining each type of hybrid. The code for the hybrids of group 1, group 2 and 3 respectively is identical in tables III and IV.

| | | | MAT α | | | |
|---|---|---|---|---|---|---|
| | | | Parental gre3Δ; — 34% | Recombinant gre3Δ; GRE3 16% | Recombinant GRE3; — 16% | Parental GRE3; GRE3 34% |
| MATa | Parental | gre3Δ; — 34% | 11.6% | 5.4% | 5.4% | 11.6% |
| | Recombinant | gre3Δ; GRE3 16% | 5.4% | 2.6% | 2.6% | 5.4% |
| | Recombinant | GRE3; — 16% | 5.4% | 2.6% | 2.6% | 5.4% |
| | Parental | GRE3; GRE3 34% | 11.6% | 5.4% | 5.4% | 11.6% |

The results presented in table V suggest that the proportion of Group 2 hybrids (italicized text) is 63.4%. At the same time, the proportion of strains of Group 2 represents 64.5% of the population. It seems therefore that in the population tested, about 1% of hybrids are starting strains that were not killed during ether enrichment.

Summary on the Construction of the Population

In summary: it was possible to build a population of strains from a single starting hybrid. It was shown that this new population, that was generated after 4 phases of bulk hybridization and sporulation, is the product of a broad genome shuffling.

Selection of Individuals of Interest in the Resulting Population

After verification of the quality of genome shuffling, resulting yeasts were selected on their ability to ferment xylose while resisting to inhibitors.

To do this, they were cultured for 48 hours on medium YFI$_1$ and then transferred for a 72-hour culture on a YFX medium. (NB. The compositions of media are shown in table I (supra) or in the text that follows the table). Samples of this second population were spread over a YEG medium (supra). This last step has led, among others, to the isolation of the strain deposited at the CNCM (Collection Nationale de Cultures de Microorganismes, Institut Pasteur, 25 rue du Docteur Roux, 75724 Paris Cedex 15) under number I-4749.

Validation of Optimized Propagation

Initially, the propagation of strains was tested on a Pref medium, and Pref+nitrogenous bases medium. This is illustrated in FIG. 1. These results indicate that:

strain I-4538, recombinant strain used for the present invention, propagates efficiently on Pref+nitrogenous bases medium, but propagates very poorly on Pref medium;

strain EGAc1 (I-4839), wild strain crossed according to the present invention with the strain I-4538, does not propagate efficiently on Pref or Pref+nitrogenous bases medium;

strain I-4749 according to the invention effectively propagates on Pref medium.

Validation of Propagation on Industrial Type Medium

Figure 2:
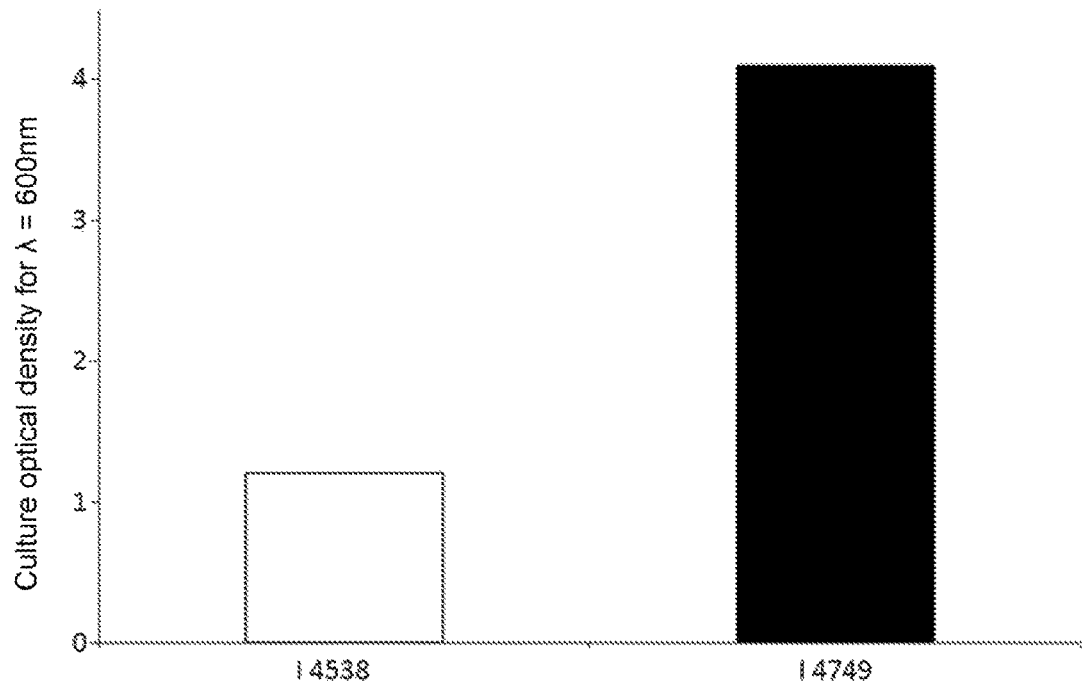
FIG. 2 shows the comparison between the propagation of the strain I-4749 according to the invention and the propagation of the parent strain I-4538 on a synthetic medium mimicking an industrial propagation medium.

A YFC medium (shown in table I supra) has been defined as mimicking the conditions of an industrial medium type mixture of hexoses (e.g. glucose, galactose, etc.) and pentoses (e.g. xylose, arabinose, etc.). The respective propagation of strains I-4538 (parent strain) and I-4749 (strain according to the invention) has been validated on this medium. FIG. 2 shows these results and demonstrates an efficiency of propagation of more than double for the strain according to the invention.

Validation of Fermentation Suitability

Figure 3:
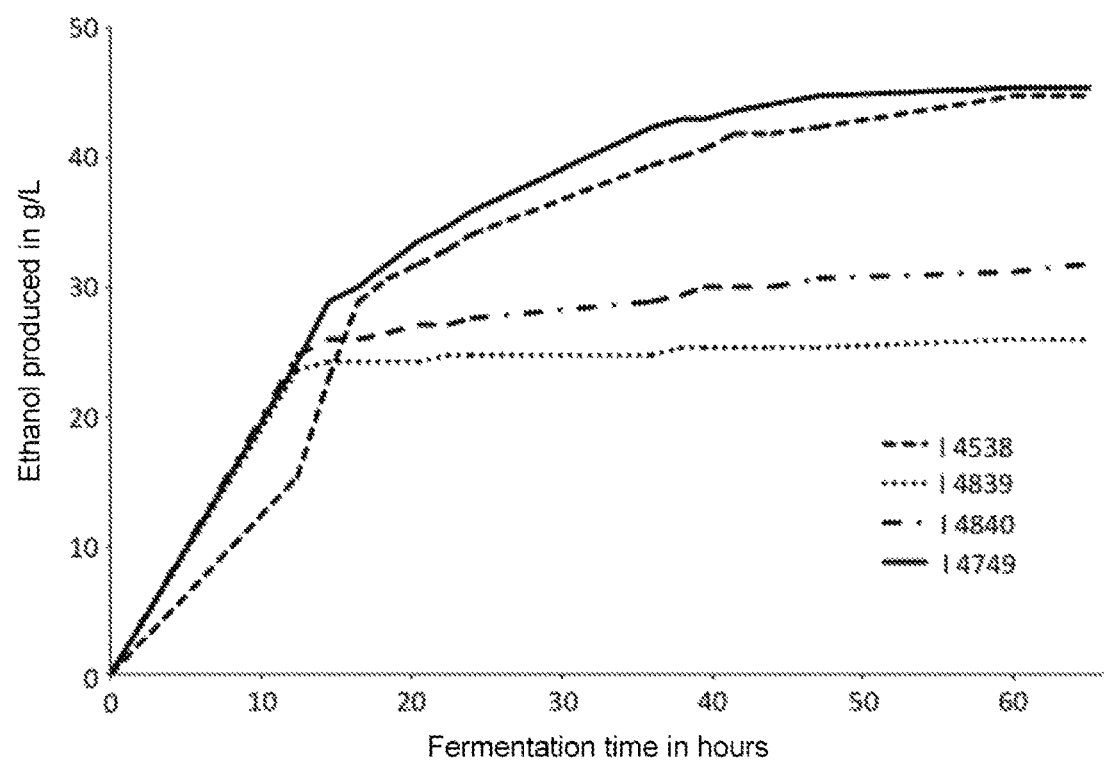
FIG. 3 shows the production of ethanol by the wild strain EGAc1 (I-4839), the recombinant parent strain I-4538 and the strain according to the invention I-4749.

The strain according to the invention has been used for fermentation in a medium close to the actual medium. The YF12 medium used for this purpose comprises both glucose and xylose so C6 and C5 sugars. The result of monitoring loss of mass during fermentation is shown in FIG. 3. In the case of all strains implemented, fermentation is biphasic.

In the first phase, strains EGAc1 (I-4839) and EGAc2 (I-4840) behave in the same way. The same goes for strain I-4749 according to the present invention. However strain I-4538 is slower during this first phase. Considering the principle of catabolite repression by glucose, it is likely that this first part of the fermentation corresponds to the consumption of glucose.

During the second phase of fermentation, it is worth noting a significant slowdown for all strains. However, the most effective strains are strains I-4538 and I-4749. This second phase probably corresponds to the consumption of xylose which is suggested by the fact that strain EGAc1 (I-4839) (of [Xylose-] phenotype) does not ferment.

The record shows that the best compromise between all strains implemented is I-4749 obtained according to the invention.

The invention claimed is:

1. Yeast comprising at least one copy of an exogenous xylose isomerase gene incorporated into the genome and linked to one of the mating traits of the strain and at least one additional D-xylulokinase gene incorporated into the genome and linked to one of the mating traits of the strain, and able to grow on a low nutritional value medium comprising a protein hydrolysate and devoid of nitrogenous bases.

2. The yeast according to claim 1, which is able to produce ethanol from xylose as the sole source of carbon.

3. Yeast according to claim 1, said yeast being of the genus *Saccharomyces*.

4. The yeast according to claim 3, said yeast being of the species *Saccharomyces cerevisiae*.

5. The yeast according to claim 4 comprising a strain deposited at the CNCM (Collection Nationale de Cultures de Microorganismes, Institut Pasteur, 25 rue du Docteur Roux, 75724 Paris Cedex 15) under number I-4749.

6. The yeast according to claim 3, further comprising at least one additional copy of the GAL2 gene.

7. The yeast according to claim 6, said yeast being of the species *Saccharomyces cerevisiae*.

8. The yeast according to claim 7 comprising a strain deposited at the CNCM (Collection Nationale de Cultures de Microorganismes, Institut Pasteur, 25 rue du Docteur Roux, 75724 Paris Cedex 15) under number I-4829.

9. The yeast strain derived from a yeast according to claim 1, characterized in that it is suited to metabolize pentoses while resisting to fermentation inhibitors.

10. Yeast resulting from culture of a yeast strain according to claim 9.

11. A process for obtaining a yeast strain suited to propagating effectively on a medium with low nutritional potential, suited to metabolize pentoses, and with fermentation inhibitor resistance, comprising the steps of:
   a) crossing a recombinant yeast strain with a wild yeast strain devoid of deficiencies, wherein the recombinant yeast strain includes at least one copy of an exogenous xylose isomerase gene and at least one additional copy of a D-xylulokinase gene incorporated into the genome and linked to one of the mating traits of the strain,
   b) performing at least two cycles of genome shuffling by random sporulation and/or hybridization,
   c) selecting a population obtained in step b)
      (i) according to a criterion of ability of strains to metabolize xylose, and
      (ii) according to a criterion of ability of the strains to grow in a medium low in nutritional value which is poor in nitrogenous bases and which comprises xylose as a sole source of carbon.

12. The process according to claim 11 wherein the recombinant yeast strain of step a) is the yeast strain deposited at the CNCM (National Collection of Cultures de Microorganismes, Institut Pasteur, 25 rue du Docteur Roux, 75724 Paris Cedex 15) under number I-4538.

13. The process according to claim 11 wherein the selecting of (c)(i) includes a step of selection on a YFX medium.

14. The process according to claim 11, wherein the selecting of (c)(i) comprises the steps of: measuring the percentage of xylose converted into ethanol by at least one hybrid, in anaerobic conditions over 60 hours in a fermentation medium comprising 55 g of glucose and 45 g of xylose per kg of said medium and selecting at least one hybrid that converts at least 70% of the xylose into ethanol in 60 hours.

15. The process according to claim 11, wherein the selecting of (c)(ii) comprises measuring the propagation of the strain on a medium low in nutritional value that comprises a protein hydrolysate and is devoid of nitrogenous bases.

16. The process according to claim 15 wherein the medium low in nutritional value comprises the following components: 1000 g/L Distilled water qs, 20 g/L Xylose, 5 g/L $(NH_4)_2SO_4$, 3 g/L Protein Hydrolysate, 0.04 g/L $ZnSO_4$, 0.5 g/L $MgSO_4 7H_2O$, 1 g/L $KH_2PO_4$, 0.1 g/L NaCl, 0.1 g/L $CaCl_2$, 0.005 g/L $H_3BO_3$, 0.06 g/L $CuSO_4$ $5H_2O$, 0.001 g/L KI, 0.004 g/L $MnSO_4 H_2O$, 0.002 g/L $Na_2MoO_4$ $2H_2O$, 0.0002 g/L $FeCl_3$, 0.07 g/L Thiamine, 0.002 g/L Pyridoxine, 0.002 g/L Biotin KOH, 0.002 g/L Pantothenate, 0.05 g/L Nicotinic Acid, 0.2 g/L Mesoinositol, 0.002 g/L Riboflavin, 0.002 g/L Para aminobenzoate.

17. The process according to claim 11, further comprising a step of genetic transformation by the addition of at least one copy of the GAL2 gene.

18. The process according to claim 11, wherein the selecting c) comprises: selecting a population according to (c)(i), and then selecting a population obtained in step (c)(i) according to (c)(ii).

19. The process according to claim 11, wherein the selecting c) comprises selecting a population according to (c)(ii), and then selecting a population obtained in step (c)(ii) according to (c)(i).

20. A method for producing ethanol comprising the steps of:
a) fermenting, in anaerobic or semi-anaerobic conditions, a medium comprising one source of xylose, by a yeast according to claim 1, and
b) obtaining ethanol.

* * * * *